US011273041B2

(12) United States Patent
Ryu (10) Patent No.: US 11,273,041 B2
(45) Date of Patent: Mar. 15, 2022

(54) SYSTEM FOR PRODUCING ARTIFICIAL OSSEOUS TISSUE AND METHOD FOR PRODUCING SAME

(71) Applicant: BIOALPHA CORPORATION, Seoul (KR)

(72) Inventor: Hyun Seung Ryu, Gyeonggi-do (KR)

(73) Assignee: BIOALPHA CORPORATION, Seoul (KR)

( * ) Notice: Subject to any disclaimer, the term of this patent is extended or adjusted under 35 U.S.C. 154(b) by 1069 days.

(21) Appl. No.: 15/539,329

(22) PCT Filed: Dec. 24, 2015

(86) PCT No.: PCT/KR2015/014240
§ 371 (c)(1),
(2) Date: Jun. 23, 2017

(87) PCT Pub. No.: WO2016/105148
PCT Pub. Date: Jun. 30, 2016

(65) Prior Publication Data
US 2017/0354502 A1    Dec. 14, 2017

(30) Foreign Application Priority Data
Dec. 24, 2014   (KR) .................. 10-2014-0188929

(51) Int. Cl.
*A61F 2/28*           (2006.01)
*A61F 2/30*           (2006.01)
(Continued)

(52) U.S. Cl.
CPC ............ *A61F 2/2846* (2013.01); *A61B 34/00* (2016.02); *A61F 2/28* (2013.01); *A61F 2/30* (2013.01);
(Continued)

(58) Field of Classification Search
CPC ......... A61F 2/2846; A61F 2/3094; C08J 3/20; B27N 3/00
See application file for complete search history.

(56) References Cited

U.S. PATENT DOCUMENTS 8,234,097 B2    7/2012  Steines et al.
2009/0149977 A1   6/2009  Schendel
(Continued)

OTHER PUBLICATIONS

Hong (Hong, S. H., & Ryu, H. J. (2003). Combination of mechanical alloying and two-stage sintering of a 93W—5.6 Ni—1.4 Fe tungsten heavy alloy. Materials Science and Engineering: A, 344(1-2), 253-260.) (Year: 2003).*

(Continued)

*Primary Examiner* — Bijan Mapar (57) ABSTRACT

The present invention relates to a system for producing artificial osseous tissue comprising: a client computer acquiring an image information of a subject bone tissue from an imaging unit that picks up an image of a subject bone tissue of a patient to generate a 3D image information; a server computer identifying the subject bone tissue based on the image information of the subject bone tissue received from the client computer, generating a 3D image information of at least one therapeutic bone tissue model corresponding to the subject bone tissue, and transmitting the 3D image information of the at least one therapeutic bone tissue model to the client computer; and a machining unit for fabricating an artificial bone tissue based on the 3D image information of the therapeutic bone tissue model determined from the server computer.

28 Claims, 4 Drawing Sheets

(51) Int. Cl.
  *A61B 34/00*  (2016.01)
  *G16Z 99/00*  (2019.01)
  *A61L 27/46*  (2006.01)
  *C04B 35/628* (2006.01)
  *C08J 3/20*   (2006.01)
  *B27N 3/00*   (2006.01)

(52) U.S. Cl.
  CPC ........ *A61F 2/3094* (2013.01); *A61F 2/30942* (2013.01); *A61L 27/46* (2013.01); *C04B 35/628* (2013.01); *C08J 3/20* (2013.01); *G16Z 99/00* (2019.02); *A61F 2002/30001* (2013.01); *A61F 2002/30948* (2013.01); *A61F 2002/30952* (2013.01); *B27N 3/00* (2013.01)

(56) References Cited

U.S. PATENT DOCUMENTS

| | | |
|---|---|---|
| 2009/0151736 A1 | 6/2009 | Belcher et al. |
| 2014/0195205 A1 | 7/2014 | Benker et al. |
| 2014/0228860 A1 | 8/2014 | Steines et al. |

OTHER PUBLICATIONS

International Search Report dated Jun. 3, 2016 for PCT/KR2015/014240.

\* cited by examiner

SYSTEM FOR PRODUCING ARTIFICIAL OSSEOUS TISSUE AND METHOD FOR PRODUCING SAME

This application claims the priority of Korean Patent Application No. 10-2014-0188929, filed on Dec. 24, 2014 in the KIPO (Korean Intellectual Property Office), the disclosure of which is incorporated herein entirely by reference. Further, this application is the National Stage application of International Application No. PCT/KR2015/014240, filed Dec. 24, 2015, which designates the United States and was published in Korean. Each of these applications is hereby incorporated by reference in their entirety into the present application.

TECHNICAL FIELD

The present invention relates to a computer guided system for surgical operation on a bone tissue, and more particularly, to a system for fabricating an artificial bone tissue for treating a subject bone tissue and a method of fabricating the same.

BACKGROUND ART

In general, when treating the loss of bone tissue due to diseases such as fractures of the bone tissue, deformities or defects due to genetic diseases, or inflammation, treatment by surgical operations such as reconstruction, replacement, or prosthesis using artificial bone tissue is preferable. For these reconstruction, replacement, or prosthesis of such a bone tissue, a suitable artificial bone tissue should be fabricated by considering the shape, size and/or position of the required bone tissue.

Conventionally, a patient's bone tissue to be treated is confirmed by naked eye or computed tomography (CT) and an imaging diagnosis device, and a bone tissue suitable for the treatment of the patient is extracted from other tissues by auto-transplantation process, or is donated from other person by heterotropic-transplantation process, and then, the bone tissue is prepared in such a manner as to be suitable for the treatment of the patient. In any case, the surgeon has precisely fabricated the replacement bone tissue and applied it to the surgery by considering factors such as general size, shape, and/or partial removal of the bone tissue depending on the disease. However, when such a bone tissue is fabricated during the surgery, it is required to have a high level of experience for the operation team, sometimes it is difficult to precisely process the bone tissue during the surgery, resulting in excessive tissue damage due to unnecessary invasion, or resulting in additional sequelae after surgery due to imprecisely fabricated replacement bone tissue. In addition, a long operation time due to in-operation manufacturing the bone tissue is also problematic.

In the case of the autotransplantation, it may cause a tissue defect of the donor portion, which leads to a problem of inducing secondary defects. Also, in the case of other heterotropic-transplantation, the donated human bone tissue bears an ethical or legal problem depending on society or culture background, and therefore its application is limited. Therefore, it is desirable to treat the patient with artificial bone tissue rather than the donated human bone tissue.

DISCLOSURE OF THE INVENTION

Technical Problem

The technical problem to be solved by the present invention is to provide a system for fabricating an artificial bone tissue and surgical guide system to fabricate the artificial bone tissue precisely and quickly, even without a high degree of experience of a medical team for treating a subject bone tissue by surgical operation and to minimizes the invasion associated with the surgical operation and shortens the time required for the surgical operation.

Another technical problem to be solved by the present invention is to provide a method of fabricating an artificial bone tissue having the above-described advantages.

Technical Solution

To solve the above problem, there is provided a system for fabricating an artificial bone tissue, the system comprising: a client computer acquiring an image information of a subject bone tissue from an imaging unit that picks up an image of a subject bone tissue of a patient to generate a 3D image information, being coupled to a network for transmitting the image information, and including a user interface for input of a user and output of an information; a server computer identifying the subject bone tissue based on the image information of the subject bone tissue received from the client computer, generating a 3D image information of at least one therapeutic bone tissue model corresponding to the subject bone tissue, and transmitting the 3D image information of the at least one therapeutic bone tissue model to the client computer so that the image information of the at least one therapeutic bone tissue model is verified and determined by the client computer; and a machining unit for fabricating an artificial bone tissue based on the 3D image information of the therapeutic bone tissue model determined from the server computer.

In one example, the system may further comprise a delivery system for delivering the artificial bone tissue fabricated by the machining unit to a hospital system. The imaging unit may include at least one of an X-ray apparatus, a computed tomography (CT) apparatus, a magnetic resonance imaging (MRI) apparatus, an optical coherence tomography apparatus, an ultrasound imaging apparatus, and a positron emission tomography (PET) apparatus.

The client computer may provide the server computer with at least one or more additional information of identification information, a disease name, and an operation method of the subject bone tissue together with the image information of the subject bone tissue, and the server computer may generate a 3D image information of the therapeutic bone tissue model by referring to the additional information together with the image information of the subject bone tissue. The server computer may include a first database for storing basic image information including image information of normal bone tissues collected from human bodies by age, gender, height, weight, or race, and the server computer may generate the 3D image information of the therapeutic bone tissue model from the basic image information.

The first database may store further information on an identification information of the normal bone tissue, a name of an associated disease, or an operation method. In addition, the first database may further store image information related to the subject bone tissue in the past of the patient or image information on the other side normal bone tissue in a bilateral symmetry relationship of the subject bone tissue.

The client computer may transmit the operation method of the subject bone tissue together with the image information of the subject bone tissue to the server computer, and the server computer may generate the 3D image information of the therapeutic bone tissue model by modifying the image information of the normal bone tissue with reference to the operation method. The server computer may include a second database for storing information on at least one of a shape, a material, a microstructure, a strength, an operation method, and an operation success rate of the artificial bone tissue.

In an example, the client computer may be configured to perform edition, comparison, or dimension measurement of a graphical object capable of simulating 3D image information of the therapeutic bone tissue model provided from the server computer through the user interface according to an operation method. In addition, the therapeutic bone tissue model may be determined when user accepts or modifies the therapeutic bone tissue model transmitted from the server computer through a result of the simulation. For this, the client computer may include at least one of an edition tool, a comparison tool, and a dimensional measurement tool of a graphic object for performing the simulation.

To solve the above other problem, there is provided computer-based surgical guide system coupled to an imaging unit for imaging a subject bone tissue to generate a 3D image information of the subject bone tissue, and including a user interface for user input or information output. In an example, the computer-based surgical guide system may comprise a therapeutic bone tissue model generation unit for acquiring a 3D image information of the subject bone tissue from the imaging unit, identifying the subject bone tissue based on the 3D image information of the subject bone tissue, and generating the therapeutic bone tissue model; a simulation execution unit for performing a verification on the therapeutic bone tissue model based a user input through a user interface or a recommendation of the therapeutic bone tissue model, and determining the 3D image information of the therapeutic bone tissue model; and a machining unit for fabricating an artificial bone tissue from the determined 3D image information of the therapeutic bone tissue model.

The verification of the therapeutic bone tissue model may be accomplished through simulation of applying the 3D image information of the therapeutic bone tissue model to the 3D image information of the subject bone tissue. The user input may include a command received from a user using at least one of a graphic object editing tool, a comparison tool, or a dimension measurement tool so as to modify the 3D image information of the therapeutic bone tissue model according to an operation method.

The recommendation of the therapeutic bone tissue model may be accomplished by reflecting an information on an operation method among at least one of image information for a pre- or post-procedure of prosthesis, reconstruction, fusion, and diseased area treatment. The therapeutic bone tissue model generation unit may access to a first database for storing a basic image information including image information of normal bone tissue collected from human bodies of each age, sex, height, body weight, or race, detect and select the 3D image information of the therapeutic bone tissue model from the basic image information, and transmits the detected and selected 3D image information of the therapeutic bone tissue model to the simulation execution unit. The simulation execution unit may output the 3D image information of the therapeutic bone tissue model to the user interface to prepare the verification.

To solve another problem, there is provided a method of fabricating an artificial bone tissue. The method may comprise generating a 3D image information of the subject bone tissue by imaging the subject bone tissue; identifying the subject bone tissue based on the 3D image information of the subject bone tissue, and generating a 3D image information of at least one therapeutic bone tissue model corresponding to the subject bone tissue; verifying an adaptiveness of the at least one therapeutic bone tissue model; determining the 3D image information of the therapeutic bone tissue model in the absence of a modification information on the 3D image information of the at least one therapeutic bone tissue model during the step of verifying; determining the 3D image information of the therapeutic bone tissue model by reflecting the modification information to the 3D image information of the therapeutic bone tissue model in the presence of the modification information; and fabricating an artificial bone tissue from the determined 3D image information of the therapeutic bone tissue model.

In addition, in the step of generating the 3D image information of the therapeutic bone tissue model, the 3D image information of the therapeutic bone tissue model may be generated by reflecting at least one of additional information on a prior or a past step of prosthesis, reconstruction, fusion, and diseased area treatment. In the step of generating the 3D image information of the therapeutic bone tissue model, the 3D image information of the therapeutic bone tissue model is generated by referring to at least one or more additional information among an identification information, a disease name, and an operation method of the subject bone tissue together with the 3D image information of the subject bone tissue. In the step of generating the 3D image information of the therapeutic bone tissue model, a first database for storing basic image information including image information of normal bone tissue collected from human bodies of each age, sex, height, body weight, or race is provided. The 3D image information of the therapeutic bone tissue model may be detected and selected from the basic image information.

The first database may further store additional information on an identification information of the normal bone tissue, a name of a related disease, or an operation method. The 3D image information of the therapeutic bone tissue model may be generated by modifying the image information of the normal bone tissue with reference to the operation method. A second database may be provided and the second database may store information on at least one of a shape, a material, a microstructure, a strength, an operation method, and an operation success rate of the artificial bone tissue. In addition, the step of verifying may include simulating the 3D image information of the therapeutic bone tissue model according to an operation method by editing, comparing, or dimension-measuring a graphic object implemented from the 3D image information. In addition, the step of determining the 3D image information of the therapeutic bone tissue model may further comprise performing learning by replacing the 3D image information of the normal bone tissue with 3D image information of the replacement bone tissue.

Advantageous Effects

According to an embodiment of the present invention, by the corporation between a server computer for identifying 3D image information of a subject bone tissue and generating 3D image information of a therapeutic bone tissue model corresponding to the subject bone tissue, and a client computer for verifying and determining the 3D image information of the therapeutic bone tissue model, the 3D image information of the therapeutic bone tissue model may be confirmed, and an artificial bone tissue may be fabricated based on the 3D image information of the therapeutic bone tissue model so that the artificial bone tissue can be fabricated accurately and promptly even without a high degree of experience of a medical team and invasion associated with the surgical operation can be minimized and the time required for the surgical operation can be shortened.

In addition, according to an example of the present invention, there can be provided a method of fabricating an artificial bone tissue having the above-described advantages.

MODE FOR CARRYING OUT THE INVENTION

Hereinafter, preferred embodiments of the present invention will be described in detail with reference to the accompanying drawings.

While the present invention has been particularly shown and described with reference to exemplary embodiments thereof, it is evident that many alternatives, modifications and variations will be apparent to those skilled in the art. It is not limited to the following described embodiment. Rather, these embodiments are provided so that this disclosure will be more thorough and complete, and will fully convey the scope of the concept of the invention to those skilled in the art.

In the following drawings, thickness and size of each element are exaggerated for convenience and clarity of description, and the same reference numerals denote the same elements in the drawings. As used herein, the term "and/or" includes any and all combinations of one or more of the listed items.

The terminology used herein is for the purpose of describing particular embodiments only and is not intended to be limiting of the invention. As used herein, the singular forms "a", "an" and "the" are intended to include the plural forms as well, unless the context clearly dictates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although the terms first, second, etc. are used herein to describe various elements, components, regions, layers and/or portions, these elements, components, regions, layers and/or portions should not be limited to the terms. It is obvious that these terms are only used to distinguish one element, component, region, layer or portion from other element, component, region, layer or portion. Thus, a first member, component, region, layer or portion described below may refer to a second member, component, region, layer or portion without departing from the teachings of the present invention FIG. 1 shows a system 100 for manufacturing an artificial bone tissue according to an embodiment of the present invention.

Figure 1:
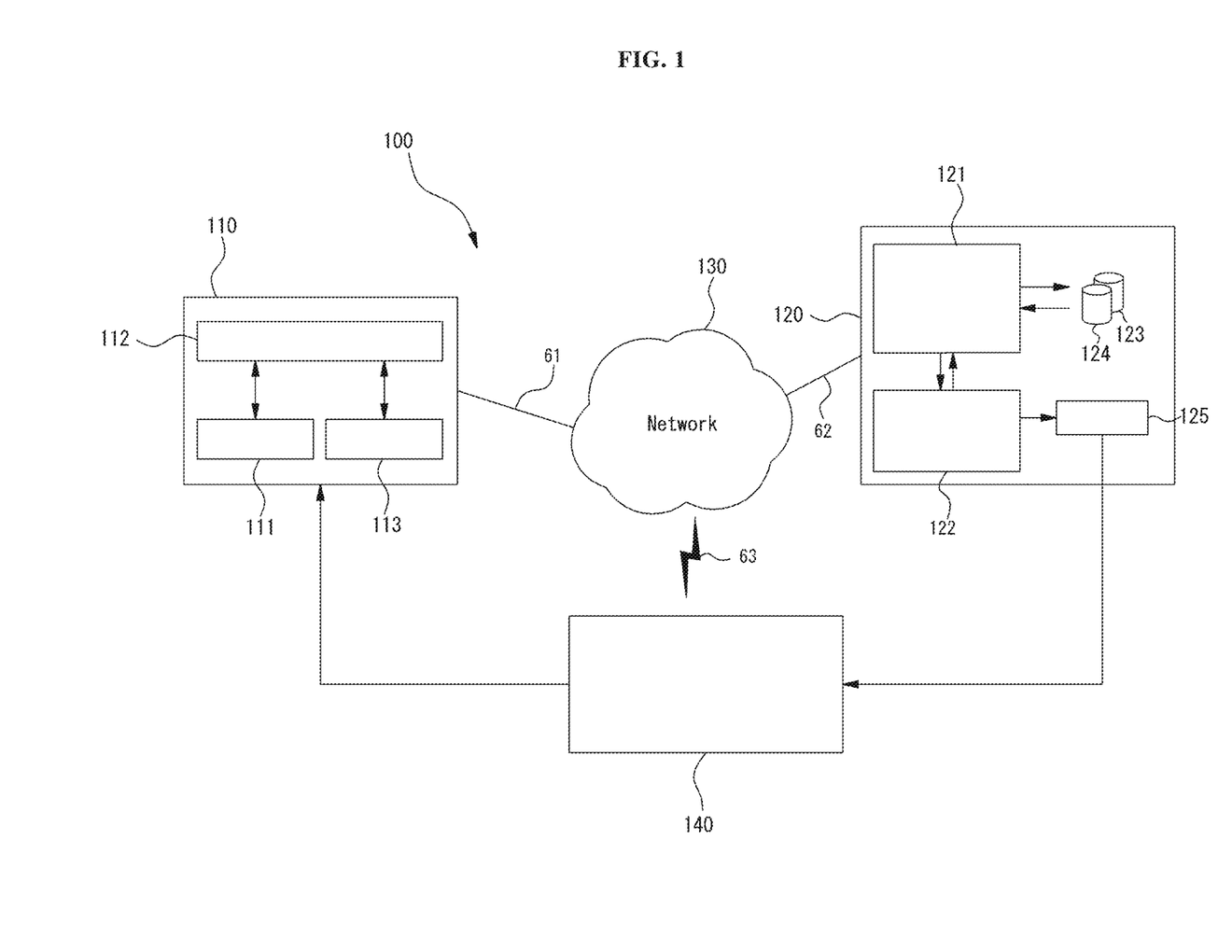
FIG. 1 shows an artificial bone tissue manufacturing system according to an embodiment of the present invention.

Referring to FIG. 1, the system 100 for manufacturing an artificial bone tissue according to the present invention may include an imaging unit 111, a client computer 112, a server computer 121, and a processing unit 122. For example, the imaging unit 111 and the client computer 112 may be installed at the operating room or the diagnostic room in the hospital system 110, and the server computer 121 and the processing unit 122 may be installed in an artificial bone tissue processing and manufacturing system 120 which is located in a site separated or different from the operating room or the diagnostic room. Each component may allow remote access to each other via network 130, as shown in FIG. 1, if desired. To this end, the client computer 112 or the server computer 121 may include a communication interface (not shown) for connecting to the network 130.

In one embodiment, there are a plurality of hospital systems 110, so that there may be a plurality of client computers 112 and imaging units 111. However, the artificial bone tissue processing and manufacturing system 120 may be single. In this case, a many-to-one relationship can be established between a plurality of hospital systems 110 and the one artificial bone tissue processing and manufacturing system 120. The plurality of client computers and the server computer may be communicably connected to each other via the network 130 including a wired/wireless communication network.

The client computer 112 or server computer 121 may comprise a persistent or temporary storage device for storing application software and data, at least one or more databases stored in the persistent or temporary storage device, and a central processing unit. As an example of the database, first and second databases 123 and 124 provided on the side of the server computer 121 are illustrated. The client computer 112 or server computer 121 may also have a user interface that includes an input, such as a mouse, keyboard, or touch panel, and an output, such as a monitor, projection display, and head-up display. The user interface may implement an augmented reality in order to improve the realism of the simulation and information transmission efficiency described later. Reference numeral 113 denotes the user interface coupled to the client computer 112.

In one embodiment, the user interface 113 of the client computer 112 may be remotely shared by the server 121. For example, when the user interface 113 is a display, image contents or information to be operated by a user on the client computer 112 may be transmitted to the server 121 and identically displayed on a display of the server 121. Similarly, image contents or information to be operated by a user on the server 121 may be transmitted to the client computer 112 and identically displayed on the display of the client computer 112 for a user on the client computer 112. The embodiment of the present invention can be realized by streaming multimedia information using the Internet or transmitting/receiving control information, but the present invention is not limited thereto.

The above-described elements of the client computer 112 or the server computer 121, the first and second databases 123 and 124 are not limited to being implemented in a single computer but may be implemented in a distributed or cloud manner. In one embodiment, the main data and executable program of the client computer 112 may be stored in the server computer 121, and the client computer 112 may download and use it. However, the present invention is not limited thereto.

The imaging unit 111 provided in the hospital system 110 may pick up an image of a patient's subject bone tissue, convert the image into an electrical signal, and transmit the electrical signal to the client computer 112. The subject bone tissue may be, for example, but not limited to, any bone tissue, such as a maxillofacial bone, a vertebra bone, a skull or a long bone of limbs which may be required to be surgically operated by partial or entire replacement, prosthesis, reconstruction, or fusion between an existing or a replacing bone tissue and an adjacent bone tissue.

The imaging unit 111 may be an imaging device capable of generating arbitrary 3D image information including information on the size, shape, position, disease or symptom of the subject bone tissue. The imaging unit 111 may include at least one of an X-ray apparatus, a CT (computed tomography) apparatus, an MRI (magnetic resonance imaging) apparatus, and a PET (positron emission tomography) apparatus. However, since the 3D image information can be generated by 3Dly rendering from a plurality of two-dimensional information, the imaging unit 111 can include an imaging device capable of generating two-dimensional image information capable of 3D rendering.

The 3D image information may include 3D image information of the subject bone tissue for replacement, prosthesis, reconstruction, or fusion for treatment of the subject bone tissue. Alternatively, 3D image information related with a wound bed preparation of a bone tissue and image information about adjacent bone tissue, muscular tissue, nerve tissue, or blood vessel tissue according to an operation method may be further included. In this specification, this information may be collectively referred to as a 3D image information of the subject bone tissue or surgical target bone tissue.

The client computer 112 may acquire the image information of the subject bone tissue via the imaging unit 111. The client computer 112 may transmit the obtained 3D image information of the subject bone tissue to the other computer via the network 130. In some embodiments, the client computer 112, may transmit, in conjunction with the image information of the subject bone tissue, information including at least one of identification information corresponding to the anatomical name of the subject bone tissue, a disease name, and a surgical procedure such as replacement, prosthesis, reconstruction and fusion to another computer via the network 130. The information on the identification information, the disease name, or the surgical procedure for the subject bone tissue can be inputted through the user interface 113 by a medical person associated with diagnosis or surgery.

The server computer 121 may receive the image information of the subject's target bone tissue transmitted from the client computer 112 through the network 130 such as the wired communication network 62. The transmitted image information may be encrypted and may further include security information that is permanently effective or can be effective only for a predetermined period of time in order to maintain the confidentiality of the transmitted image information.

Alternatively, the server computer 121 may store, together with the image information, identification information corresponding to the anatomical name of the subject bone tissue, body information (for example, but not limited to, age, age, sex, height, bone mineral density, anamnesis, disease name), and/or operation method.

The server computer 121 refers to at least one of the image recognition using the 3D image information of the subject bone tissue, and at least one information of the identification information, the body information, the disease name, and the operation method, so as to identify the subject bone tissue and, then, generate a 3D image information of the therapeutic bone tissue model corresponding to the subject bone tissue. The 3D image information of the therapeutic bone tissue model may be single or plural. The user may select any suitable one from the generated 3D image information of the therapeutic bone tissue model. The image information of the therapeutic bone tissue model generated by the server computer 121 may include information on shape, size, and location to reconstruct iliac bone of oral and maxillofacial bone, vertebra, skull, or limbs as non-limiting examples by the artificial bone tissue according to the treatment method of the subject bone tissue of any or all of the following: replacement, prosthesis, reconstruction, or any fusion of existing or replacement bone tissue and adjacent bone tissue.

Alternatively, the server computer 121 may further generate at least one additional information of identification information, disease name, and operation method corresponding to the image information of the therapeutic bone tissue model. At least one of the identification information, disease name, and operation method information generated by the server computer 121 may be used an guide information for recommending a diagnosis, a treatment, or a surgery method by a user (or a medical doctor) of the server computer 121, May match or be inconsistent with information on the identification information, the disease name, or the operation method transmitted from the client computer 110 as input by the user. When the information is consistent with each other, the user can be assured of the determination, and when the information is inconsistent, the information can be used as the proposal information provided by the system.

The server computer 121 may store in the first database 123 of the permanent storage device or the temporary storage device for storing the data, a 3D image information of the therapeutic bone tissue model and optionally basic image information for generating an additional information. The basic image information may include image data of normal bone tissue collected from human bodies of each age, sex, height, body weight, or race, and optionally includes identification information of the normal bone tissue, a name of associated disease or operation method.

The server computer 121 may detect the image information of the normal bone tissue corresponding to the 3D image information of the subject bone tissue from the basic image information based on the 3D image information of the subject bone tissue received from the client computer 112. In addition, the server computer 121 may detect the additional information in connection with the identification information of the normal bone tissue, the name of the related disease, or the operation method together with the image information of the detected normal bone tissue. The server computer 121 may combine the detected 3D image information of the normal bone tissue and optionally additional output information with the 3D image information of the subject bone tissue so that the server computer 121 may generate 3D image information of the therapeutic bone tissue model.

In some embodiments, if there is image information about the prior or past steps of prosthesis, reconstruction, fusion, or diseased area treatment as an additional information about the surgical procedure for the therapeutic bone tissue received from the client computer 112, the server computer 121 may reflect the additional information to the image information of the normal bone tissue by referring to the additional information so that the server computer 121 may modify a shape, a size or a position of the normal bone tissue to generate the 3 dimensional image information of the therapeutic bone tissue model based on the modified image information of the normal bone tissue. For example, when the operation method of the subject bone tissue received from the client computer 112 is prosthesis or fusion, since the operation is not performed by completely replacing the normal bone tissue with the artificial bone tissue, modification on a part or entirety of the image information of the normal bone tissue may be required, the 3D image information of the therapeutic bone tissue model based on the modified image information of the normal bone tissue may be generated.

In another embodiment, the 3D image information of the normal bone tissue may be image information on the patient's own past subject bone tissue or image information on the other normal bone tissue in a bilateral symmetry relationship with respect to the subject bone tissue. The image information of the normal bone tissue of the patient himself may be utilized for the server computer 121 to identify the subject bone tissue and generate the 3D image information of the therapeutic bone tissue model. For example, when the server computer 121 fails to detect the image information of the normal bone tissue corresponding to the 3D image information of the subject bone tissue, or there is a purpose for an independent and separate reference, the server computer 121 may generate a 3D image information of an alternative therapeutic bone tissue model and then transmit the 3D image information to the client computer 112 so that the client computer 112 may easily compare the 3D image information of the subject bone tissue with the 3D image information of the therapeutic bone tissue model to modify the 3D image information of the therapeutic bone tissue model easily.

Together with the 3D image information of the therapeutic bone tissue model based on the image information of the normal bone tissue, the additional information, or the modified normal bone tissue, the server computer 121 may generate an information for an artificial bone tissue including shape, material, microstructure, strength, operation method, and surgical success rate of the artificial bone tissue when the artificial bone tissue is implemented with the artificial bone tissue. Basic information of the artificial bone tissue such as the material, the microstructure, the strength or the success rate of the operation for the artificial bone tissue can be stored and managed in the second database 124, and the information about the generated therapeutic bone tissue model can be also stored in the second database 124). The material, the microstructure, the strength or the surgical success rate of the artificial bone tissue stored and managed in the second database 124 may be modified by the user or reflected to by further information on user preference.

In the above-described examples, the first data base 123 in which the information on the normal bone tissue for deriving the therapeutic bone tissue model may be recorded, and the second data 124 in which the information on the generated therapeutic bone tissue model and/or the artificial bone tissue may be implemented respectively as separate databases, as shown in FIG. 1. However, these are exemplary only and may be implemented in a single database or multiplexed into a distributed or cloud system, but is not limited thereto.

The information of at least one of the 3D image information of the bone tissue model generated by the server computer 121 and optionally shape, material, microstructure, strength, operation method and surgical success rate of the artificial bone tissue may be transmitted to the wired communication network 62 to the client computer 112 via a network 130. The client computer 112 may receive the information generated by the server computer 121 and provide or recommend the information to a user (e.g., a physician) through a user interface 113 such as a graphic interface, e.g., a display device.

The user may read the 3D image information and the related additional information of the provided and recommended therapeutic bone tissue model through the user interface 113 of the client computer 112. The client computer 112 may have a dedicated program or software module such as editor tools for 3D movement, rotation, symmetry, cropping, partial creation, enlargement/reduction of a graphical object, comparison tools between different graphical objects or dimensional measurement tools for a user to implement a simulation on the user interface 113 according to an operation methods such as prosthesis, reconstruction or fusion by using the 3D image information of the subject bone tissue received from the imaging unit 111 and the therapeutic bone tissue model received from the server computer 121. The user may modify and store the 3D image information of the subject bone tissue and/or the 3D image information of the therapeutic bone tissue model received from the server computer 121 through the dedicated program or software.

Through the user interface of the client computer 112, the user may accept or recognize the 3D image information of the therapeutic bone tissue model provided and recommended from the server computer 120, when the 3D image information of the therapeutic bone tissue model provided and recommended from the server computer 120 is considered to be proper by the user based on the result of the above disclosed simulation. In addition, as explained above, when it is required to modify the 3D image information of the therapeutic bone tissue model for a treatment to a patient, a 3D image information of the modified therapeutic bone tissue model may be generated by reflecting a modification information defined by the user during the simulation process.

As described above, when the user accepts the 3D image information of the therapeutic bone tissue model as provided and recommended by the server computer 120, or when the user modifies the 3D image information of the therapeutic bone tissue model and then a modified 3D image information of the therapeutic bone tissue model is generated and finally the user accepts the modified 3D image information, a 3D image information of the therapeutic bone tissue model for a subject bone tissue may be determined, the 3D image information of the therapeutic bone tissue model may be transformed into a 3D image information for an artificial bone tissue to be fabricated. Optionally, together with the 3D image information of the artificial bone tissue, at least one of additional information, such as material, micro-structure, strength, and surgery method may be determined.

The server computer 121 may learn an information that has been accepted or modified by the user in association with the image information of the normal bone tissue stored in advance in the first database 123, and accordingly improve accuracy and reliability of the image information of the therapeutic bone tissue model provided and recommended by server computer 120 on the basis of the learning. An algorithm for this learning may be based on a codebook of a neural network or vector quantizer as a non-limiting example. The algorithm for learning can be personalized or shared for each user, thereby improving the accuracy of detection of 3D image information of a next therapeutic bone tissue model and reducing the time required.

The determined 3D image information of the artificial bone tissue may be stored in the database 124 in any digital format that can be decoded by a machining unit 122 described later, or may be stored in various formats of 3D image information which may be supported by a commercial software, such as, but not limited to, Autocad™, Catia™, Solidworks™, MIMICS™, or 3D MAX™.

The machining unit 122 may receive an image information the artificial bone tissue or optionally an additional information such as material and strength of the artificial bone tissue stored in the second database 124 of the server computer 121, and machine a 3D artificial bone tissue 125 on the basis the image information or optionally the additional information. For example, the machining unit 122 can machine the artificial bone tissue 125 by relatively moving a machining tool and table in three dimensionally based on the image information or optionally the additional information. The machining for the artificial bone tissue 125 may be performed by a milling method using a commercial milling machine. If necessary, a four-axis or five-axis milling machine or a dental prosthesis processing machine capable of multi-axis machining may be utilized to realize various curved surfaces of the artificial bone tissue 125.

In one embodiment, the machining unit 122 may form the artificial bone tissue 125 directly by using a machining tool, or alternatively by forming a preliminary artificial bone tissue and then machining the preliminary artificial bone tissue and performing a main sintering process on the preliminary artificial bone tissue. The strength of the preliminary artificial bone tissue may be weaker than that of the artificial bone tissue 125, and then an artificial bone tissue 125 having an enough strength that can be used for a human body by the main sintering process.

In the case of forming the artificial bone tissue 125 using the preliminary artificial bone tissue, the second database 124 of the server computer 121 may further include information on the contraction ratio of the sintered body in the present sintering process, and the machining unit 122 may use the information. The information on the shrinkage ratio of the sintered body can be variously considered depending on the characteristics of the material. For example, when the preliminary artificial bone tissue is made from hydroxyapatite (HA), the contraction ratio may be 5 to 30% over all sides of the preliminary artificial bone tissue.

In addition, various 3D printers can be used for realizing a complex shape of the artificial bone tissue 125. The artificial bone tissue 125 may be directly printed by using a 3D printer. In one embodiment, a mold part (not shown) for forming the artificial bone tissue 125 may be three-dimensionally printed and a curable compound may be filled inside the printed mold part to form the artificial bone tissue 125. After the artificial bone tissue 125 is formed according to the above-described method, the mold part can be removed from the outer surface of the artificial bone tissue 125. In this case, the second database 124 of the server computer 121 may further include 3D shape and thickness information of the mold part.

In one embodiment, the curable compound may be a calcium phosphate-based compound, and the calcium phosphate-based compound may comprise a liquid phase and a powdered solid phase containing at least one solid compound of calcium and/or phosphate. When the liquid phase and the powdered solid phase are mixed at a suitable ratio, one or more other solid compound may be precipitated to form a paste that may be cured at a room temperature or at a body temperature, wherein at least one of the solid compounds may be calcium phosphate.

The solid calcium phosphate compound may be selected from the group consisting of hydroxyapatite (HA), $Ca_{10}(PO_4)_6(OH)_2$; amorphous calcium phosphate (ACP), $Ca_x(PO_4)2H_2O$; monocalcium phosphate monohydrate (MCPH), $CaH_4(PO_4)2H_2O$; Dicalcium phosphate dihydrate (DCPD) or brushite, $CaHPO_4.2H_2O$; dicalcium phosphate anhydride (DCPA), $CaHPO_4$; precipitated or calcium deficient apatite (CDA); α- or β-tricalcium phosphate (α-TCP, β-TCP), $Ca_3(PO_4)_2$; tetra calcium phosphate (TTCP), $Ca_4P_2O_9$; and calcium carbonate $CaCO_3$. In one embodiment, the powdered solid calcium phosphate-based compound is a mixture of calcium and/or hydroxyapatite (HA), α-TCP, β-TCP, ACP, MCPH, DCPA, CDA, $CaCO_3$, and the like.

In another embodiment, the powdered solid phase may further comprise at least one synthetic polymer or a biopolymer such as hydroxypropyl methylcellulose (HPMC). Preferably, a powdered solid phase may comprise α-TCP. The α-TCP may be easily converted from aqueous solution to calcium-deficient hydroxyapatite (CDA), and apatite CPCs may be formed using this property.

The artificial bone tissue 125 may include a biocompatible polymer based, metal based, ceramic based material or two or more thereof, such as, but not limited to, hydroxyapatite, bioactive glass, β-tricalcium phosphate, dicalcium phosphate dihydrate, titanium or its alloying material (Ti6Al4V Extra Low Interstitial), Polyetheretherketone (PEEK) or ceramic composite of PEEK/calcium phosphate. These materials may be designated by the user. For example, the artificial bone tissue 125 may have various materials and microstructures depending on the required human body characteristics.

The machining unit 122 may, in another embodiment, use a mold to produce the artificial bone tissue 125. Optionally, the machining unit 122 may supply additional energy by pressing or heating, or perform a chemical treatment process such as oxidation or reduction to the artificial bone tissue 125. In addition, the artificial bone tissue 125 produced by the machining unit 122 may be sterilized or antibacterial processed, and may be packaged in a suitable manner for delivery.

The packaged artificial bone tissue 125 may be delivered to the hospital system 110 for operation of the patient by a delivery system 140 that can maintain a suitable storage state for the artificial bone tissue 125. The delivery system 140 may be connected to the hospital system 110 and an artificial bone tissue manufacturing system 120 via a wireless communication network 63, for example, as a non-limiting example of an accessible network, may be coupled to an overland transportation device, air transportation or marine transportation devices to quickly and accurately deliver the artificial bone tissue fabricated in the artificial bone tissue manufacturing system 120 to the hospital system 110.

Figure 2:
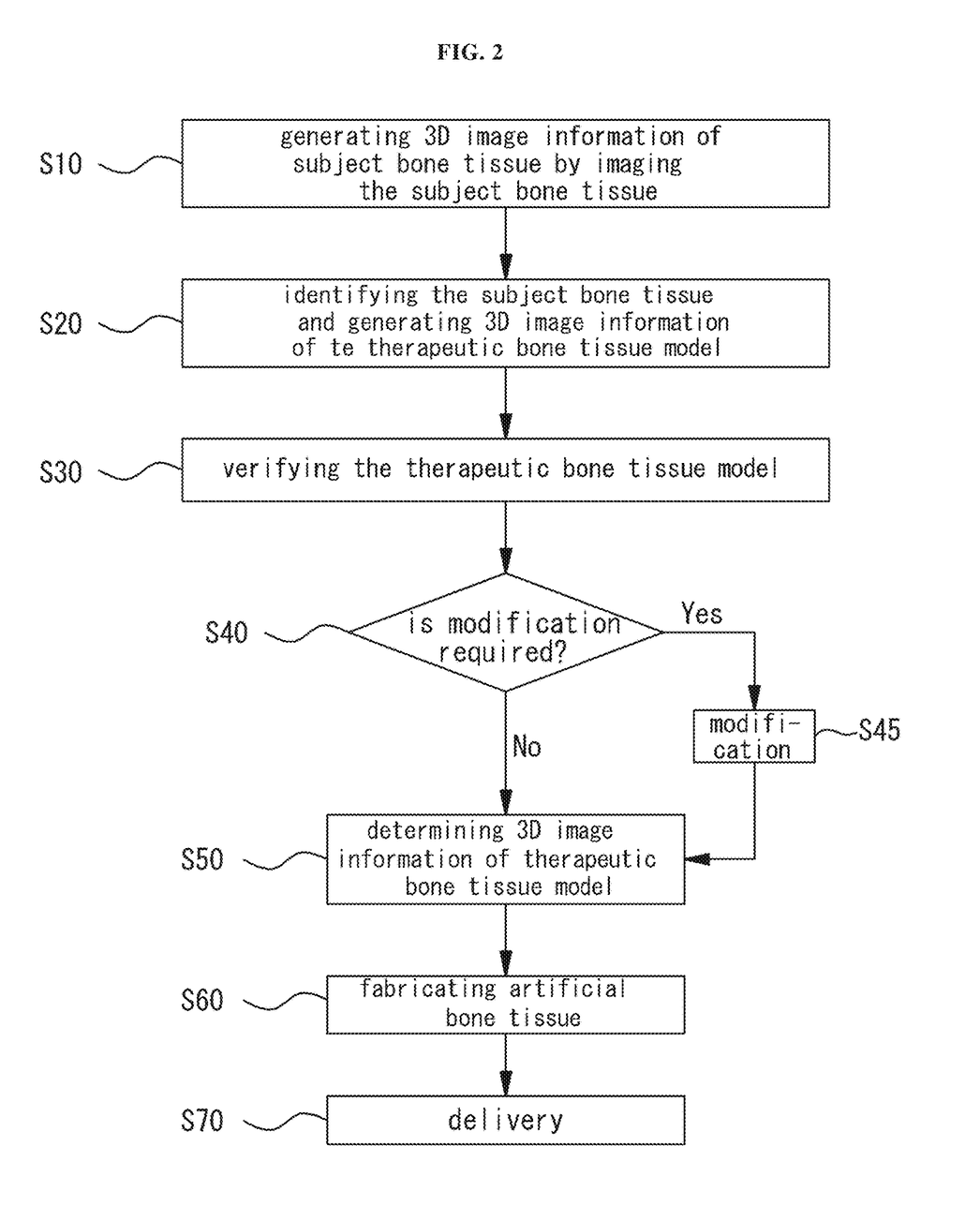
FIGS. 2 and 3 are flowcharts illustrating a method of manufacturing an artificial bone tissue according to an embodiment of the present invention.
Figure 3:
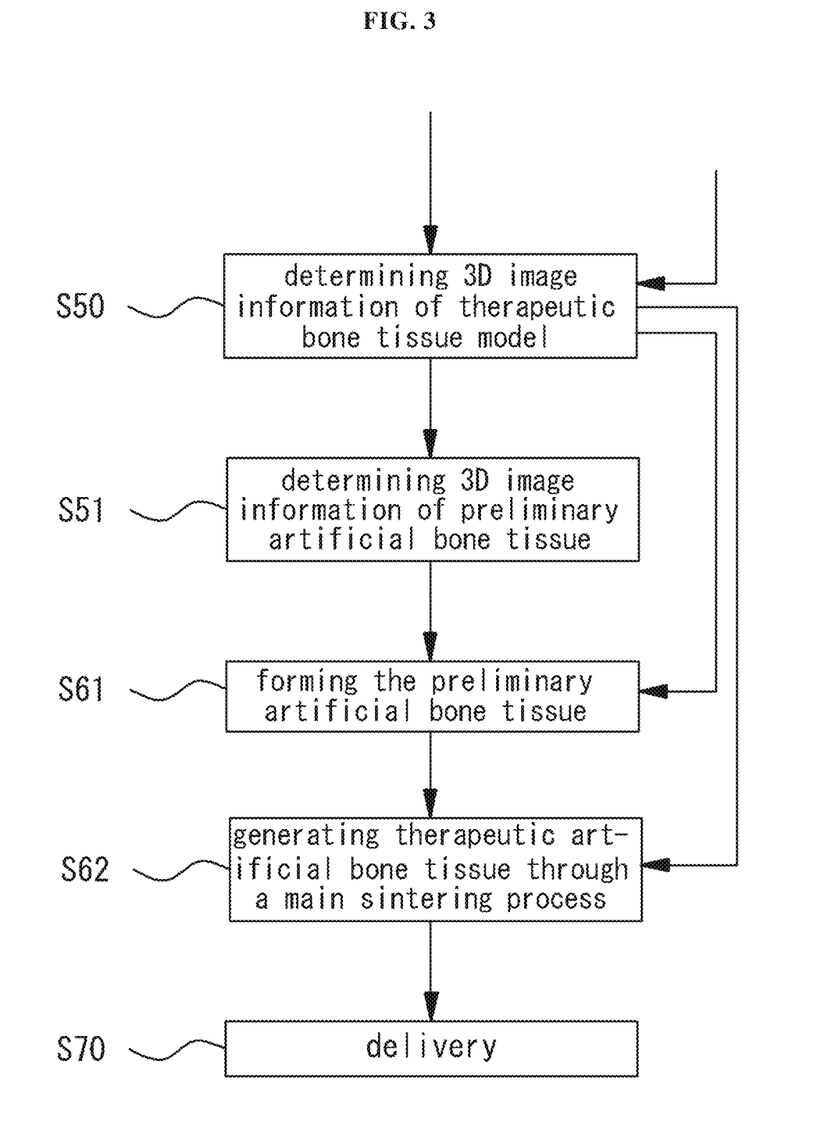

FIGS. 2 and 3 are flowcharts illustrating a method of manufacturing an artificial bone tissue according to an embodiment of the present invention.

Referring to FIG. 2, a 3D image information of the subject bone tissue may be generated by taking an image of a subject bone tissue by a 3D imaging device such as an X-ray device, a CT device, an MRI device, and PET device (S10). The 3D image information of the subject bone tissue may be as a 3D graphical data to be converted into any data in any digital format suitable for making a data and/or editing by a series of identification, editing, or measurement.

Thereafter, the subject bone tissue may be identified, and a 3D image information of the therapeutic bone tissue model corresponding to the subject bone tissue may be generated (S20). The identification of the subject bone tissue may be performed by an image recognition through comparison against a 3D image information of the normal bone tissue. In another embodiment, by replacing the image recognition or accompanying the image recognition, the identification of the subject bone tissue may be performed by referring to at least one of an identification information related with anatomical name of the subject bone tissue, a body information, a disease name, and an operation method.

After the subject bone tissue is identified, a 3D image information of at least one therapeutic bone tissue model corresponding to the subject bone tissue may be generated (S20). Referring to FIG. 1, as described above, the 3D image information of the therapeutic bone tissue model may be detected and selected from a data base in which a basic image information is stored and may include image information on various normal bone tissues collected from various human bodies by age, sex, height, weight and race. In another embodiment, the 3D image information of the therapeutic bone tissue model may be detected and selected from a data base including at least one of image information of the patient's past bone tissue or image of the normal bone tissue of the opposite side (for example, one side of a left side and right side) of the patient's body.

Subsequently, verification may be performed to determine whether the generated therapeutic bone tissue model is suitable for the treatment of the subject bone tissue according to the operation method such as substitution, prosthesis, reconstruction, or fusion of the subject bone tissue (S30). For the verification, the 3D image information of the therapeutic bone tissue model and the 3D image information of the subject bone tissue may be compared with each other, and the sameness or suitability between them may be determined.

In another embodiment, the verification may be accomplished through a simulation of applying the 3D image information of the therapeutic bone tissue model to the 3D image information of the subject bone tissue according to the operation method. In order to perform the above-described verification, dedicated programs or software modules, such as editing tools for enabling a 3D movement, rotation, symmetry, cropping, partial generation, enlargement/reduction and the like of the graphic objects, comparison tools between the graphic objects or dimension measurement tools of the graphic objects implemented with the 3D image information of the subject bone tissue and the 3D image information of the therapeutic bone tissue model may be provided, such as editing tools, comparison tools between graphic objects, or dimensional measurement tools. The user may perform simulation through a suitable user interface using these modules, and appropriate modification information for the 3D image information of the therapeutic bone tissue model may be generated.

In the verification step S30, if there is a modification item to the generated therapeutic bone tissue model, the modification information may be reflected in the 3D image information of the therapeutic bone tissue model (S45), and the 3D image information of the therapeutic bone tissue model may be determined (S50). If there is no modification item for the generated therapeutic bone tissue model, the 3D image information of the proposed therapeutic bone tissue model will be determined as it is recommended (S50). In some embodiments, a 3D image of a normal bone tissue stored in the database may be modified according to the modification information, and a learning algorithm may be performed through the alternative bone tissue image.

When the 3D image information of the therapeutic bone tissue model is determined as described above, a 3D image information of an artificial bone tissue to be fabricated may be generated, and an artificial bone tissue may be fabricated based on the 3D image information. Examples of the artificial bone tissue include, but not limited to, hydroxyapatite, bioactive glass, β-tricalcium phosphate, dicalcium phosphate dihydrate, Metal-based, ceramic-based materials having a biocompatibility such as an alloy material (Ti6Al4V Extra Low Interstitial), a polyetheretherketone (PEEK) or a PEEK/calcium phosphate-based ceramic composite, or a composite material of two or more thereof. For example, in the case of an artificial disc, the a center portion including a polyurethane core may be prepared, a biocompatible metal such as titanium may be coated on upper and lower portions of the center portion, and finally the artificial disc may be fabricated. These artificial bone tissues may be made of various materials depending on the bone tissue characteristics of the human body.

The artificial bone tissue may be sterilized after it is fabricated. In addition, when the artificial bone tissue is fabricated at a remote location, it can be delivered to the hospital for treatment of the patient by an appropriate delivery system (S70). The delivered artificial bone tissue (for example, an artificial disk) can be implanted or prosthodontically implanted in a subject bone tissue by a user (physician) located on the patient's neck or waist.

According to the embodiment of the present invention described above, it is possible to fabricate fast and economically an artificial bone tissue having suitable shape, size and/or location in response to an operation method, such as replacement, prosthesis, or reconstruction for a portion of or entire subject bone tissue to be treated, or fusion between adjacent bone tissues, which are required to be treated due to a disease such as fracture, genetic deficiency or inflammation. In addition, since the artificial bone tissue is able to be fabricated quickly and inexpensively according to the present invention, the operation time may be shortened, and a treatment result by the minimally invasive treatment can be achieved by virtue of the appropriate simulation. In addition, the above-described fabricating method may share computer resources for generating a therapeutic bone tissue model by constituting multi-to one relation between a hospital system in which a client computer is provided and a manufacturing system in which a server computer is provided, and accumulate the treatment results so as to enhance the success rate and reliability of recommendation function of the system.

In another embodiment of the present invention, as described with reference to FIG. 1, a preliminary artificial bone tissue may be formed first, and then processed to form an artificial bone tissue.

Referring to FIG. 3, when the 3D image information of the therapeutic bone tissue model is determined (S50), step for determining the 3D image information for forming the preliminary artificial bone tissue is further determined using the 3D image information (S51). The 3D image information for forming the preliminary artificial bone tissue may be determined from the 3D image information of the therapeutic bone tissue model by considering material of the preliminary artificial bone tissue and shrinkage ratio of the material in an additional process. The shrinkage ratio should be determined in consideration of sintering conditions and materials of the preliminary artificial bone tissue.

The preliminary artificial bone tissue may be fabricated using the 3D image information of the determined therapeutic bone tissue model and the 3D image information for forming the preliminary artificial bone tissue (S61). Since the preliminary artificial bone tissue is sintered by performing the first heat treatment at a relatively low temperature, it may have a weaker strength than the therapeutic artificial bone tissue. Therefore, it is possible to reduce the damage of the bone tissue during a molding process, and it is easy to be machined into a desired shape.

The preliminary artificial bone tissue formed through the first or primary heat treatment and the molding process may be fabricated into a therapeutic artificial bone tissue through a main sintering process (S62). Since the primary processed preliminary artificial bone tissue is modeled according to the 3D image information by considering the shrinkage ratio by the main sintering process, the therapeutic artificial bone tissue formed through the main sintering process may be molded to correspond to the 3D image information in the step (S50) of determining the 3D image information. The main sintering process may include a second heat treatment at a temperature higher than that of the first heat treatment and then a slow cooling for sintering the second heat treated artificial bone tissue while slowly lowering the temperature.

In one embodiment, the first heat treatment may be performed at 400° C. to 800° C., and the second heat treatment step may be performed at 700° C. to 1,300° C. After the first heat treatment at 700° C. and the second heat treatment at 1,000° C., the shrinkage ratio of each side of the preliminary artificial bone tissue was examined as follows.

TABLE 1

| Shrink ratio After the second heat treatment | X axis (%) | Y axis (%) | Z axis (%) | Volume (%) |
| --- | --- | --- | --- | --- |
| 1,000° C. | 18.64 ± 0.89 | 18.47 ± 0.15 | 17.97 ± 0.2 | 45.58 ± 0.77 |

According to Table 1, it can be confirmed that the preliminary artificial bone tissue shrinks uniformly in all directions when the second heat treatment is performed, and exhibits a shrinkage ratio of about 18%. The shrink ratio may be included in the 3D image information for forming the preliminary artificial bone tissue to be taken into account when forming the preliminary artificial bone tissue.

Figure 4:
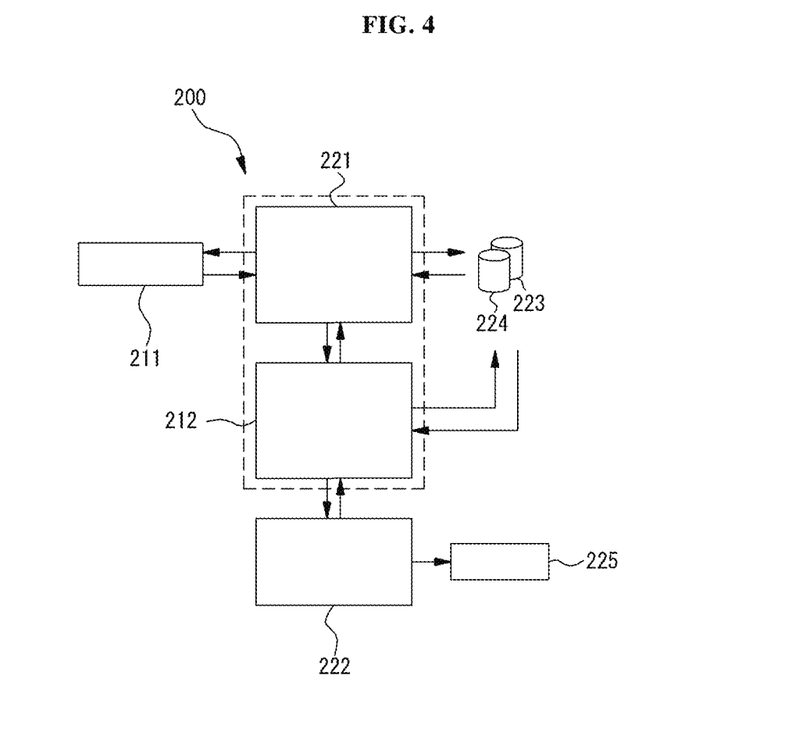
FIG. 4 is a block diagram of a computer-based guide system for surgical operation using an artificial bone tissue according to an embodiment of the present invention.

FIG. 4 is a block diagram of a computer-based surgical guide system 200 using an artificial bone tissue according to an embodiment of the present invention.

Referring to FIG. 4, the guide system 200 may include a therapeutic bone tissue model generation unit 221, a simulation execution unit 212, and a processing unit 222. These elements 221, 212, and 222 may be implemented by a single computer or a plurality of computers. The rectangular dotted line illustrates that the generating unit 221 of the therapeutic bone tissue model and the simulation execution unit 212 may be implemented by a single computer.

When these elements are implemented by the plurality of computers, a client-server relationship may be established between the pluralities of computers as described with reference to FIG. 1. At least one or more databases 223 and 224 may be provided together with the computers. These components may be present in one hospital or distributed to hospitals and artificial bone tissue manufacturers, but the present invention is not limited thereto.

The therapeutic bone tissue model generation unit 221 may acquire 3D image information of the subject bone tissue from the imaging unit 211, identify the subject bone tissue based on the 3D image information of the subject bone tissue, and generate the 3D image information of the therapeutic bone tissue model corresponding to the subject bone tissue. The therapeutic bone tissue model generation unit 221 may serve as a server computer, and in this case a client computer for transmitting the 3D image information of the subject bone tissue acquired from the imaging unit 211 to the therapeutic bone tissue model generation unit 221 may be disposed between the imaging unit 211 and the therapeutic bone tissue model generation unit 221.

The therapeutic bone tissue model generation unit 221 may be connected to a first database 223 storing basic image information including image information of normal bone tissue collected from human bodies by age, sex, height, body weight, or race, detect and select a 3D image information of the therapeutic bone tissue model from the basic image information, and then transmit the detected 3D image information of the therapeutic bone tissue model to the simulation execution unit 212.

The information about the artificial bone tissue of at least one of the shape, material, microstructure, strength, operation method, and surgical success rate of the artificial bone tissue may be generated when the therapeutic bone tissue model is implemented with an artificial bone tissue having a shape substantially identical to that of the therapeutic bone tissue model. The basic information of the artificial bone tissue such as the material, the microstructure, the strength or the success rate of the operation of the artificial bone tissue may be stored and managed in the second database 224, and the information about the generated therapeutic bone tissue model may be stored in the second database 224. The material, microstructure, strength or surgical success rate of the artificial bone tissue stored and managed in the second database 224 may be modified by the user or further information on the preference may be further reflected.

The simulation execution unit 212 may access to the therapeutic bone tissue model generation unit 221 to receive the 3D image information of the therapeutic bone tissue model to perform the verification of the therapeutic bone tissue model. The verification may be achieved through simulation of applying the 3D image information of the therapeutic bone tissue model to the 3D image information of the subject bone tissue. For this, the verification may be performed based on a user's input through a user interface for user input or information output, or a recommendation of the therapeutic bone tissue model generation unit 221. When the verification is completed, the 3D image information of the therapeutic bone tissue model may be determined. In some embodiments, in the step of verifying, when there is a modification item to the 3D image information of the therapeutic bone tissue model, the result may be stored in a database and reflected in a subsequent recommendation by a learning algorithm.

The user input may include a command received from a user using at least one of a graphic object editing tool, a comparison tool, or a dimension measurement tool so as to modify the 3D image information of the therapeutic bone tissue model according to an operation method. The recommendation of the therapeutic bone tissue model may be achieved by reflecting information on at least one of the operation methods of prosthesis, reconstruction, fusion, and image information on the prior or past steps of the treatment of the treated part of a patient's body.

The machining unit 222 may fabricate an artificial bone tissue 225 from the determined 3D image information of the therapeutic bone tissue model. The fabricated artificial bone tissue 225 may be delivered to the hospital for treatment of the patient through sterilization and package process.

Figure 5:
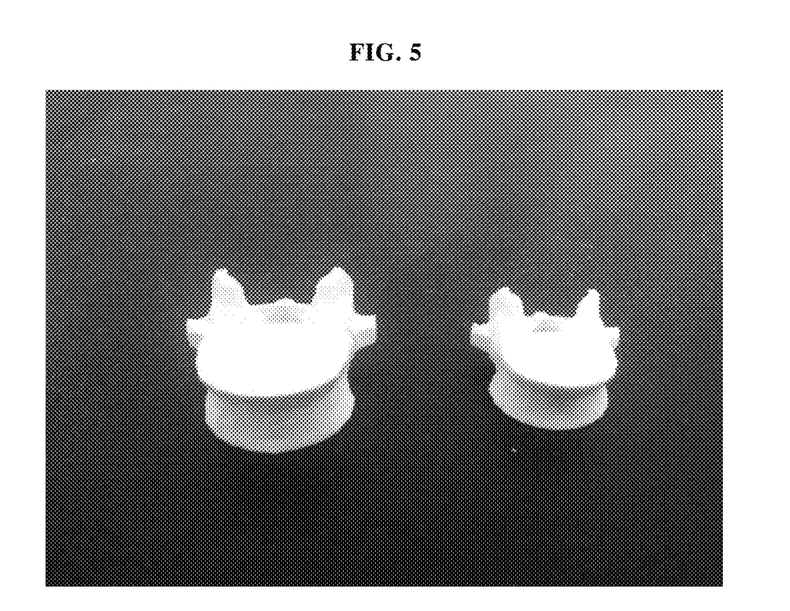
FIG. 5 is an image of a spinal-shaped preliminary artificial bone tissue (left) and a final artificial bone tissue (right) fabricated according to a manufacturing method according to an embodiment of the present invention.

FIG. 5 is an image of a spinal-shaped preliminary artificial bone tissue (left) and a final artificial bone tissue (right) fabricated according to a method of fabricating the artificial bone tissue according to an embodiment of the present invention. As described above with reference to FIGS. 2 and 3, when comparing the primary artificial bone tissue fabricated by a preliminary sintering step at a first heat treatment temperature and then a machining step with the artificial bone tissue fabricated by a main sintering step at a second heat treatment temperature, it can be confirmed that it shrinks uniformly in all directions. Thus, it can be seen that customized mass production of artificial bone tissue is possible by using the fabrication system and fabrication method of an artificial bone tissue according to an embodiment of the present invention.

It will be apparent to those skilled in the art that various modifications and variations can be made in the present invention without departing from the spirit or scope of the invention. It will be clear to those with knowledge.

The invention claimed is:

1. A system for fabricating an artificial bone tissue, the system comprising:
  a client computer acquiring an image information of a subject bone tissue from an imaging unit that picks up an image of a subject bone tissue of a patient to generate a 3D image information, being coupled to a network for transmitting the image information, and including a user interface for input of a user and output of an information;
  a server computer identifying the subject bone tissue based on the image information of the subject bone tissue received from the client computer, generating a 3D image information of at least one therapeutic bone tissue model corresponding to the subject bone tissue, and transmitting the 3D image information of the at least one therapeutic bone tissue model to the client computer so that the image information of the at least one therapeutic bone tissue model is verified and determined by the client computer; and
  a machining unit for fabricating an artificial bone tissue based on the 3D image information of the therapeutic bone tissue model determined from the server computer,
  wherein the client computer is configured to provide the server computer with a first additional information of a first identification information, a first disease name, and a first operation method of the subject bone tissue together with the image information of the subject bone tissue, the first additional information includes all of the first operation method, the first identification information, and the first disease name, and the first additional information is inputted by the user,
  wherein the server computer is configured to generate a second additional information of a second identification information, a second disease name, and a second operation method which correspond to the 3D image information of the therapeutic bone tissue model, the second additional information includes all of the second operation method, the second identification information, and the second disease name, and the second additional information is generated based on the generated 3D image information of the therapeutic bone tissue model,
  wherein the system is configured to provide the user with a comparison result between the first additional information and the second additional information, the comparison result including whether or not there is a match between the first additional information and the second additional information, and the comparison result is used as guide information for recommending a treatment and surgery method for the user.

2. The system for fabricating an artificial bone tissue of claim 1, further comprising a delivery system for delivering the artificial bone tissue fabricated by the machining unit to a hospital system.

3. The system for fabricating an artificial bone tissue of claim 1, wherein the imaging unit includes at least one of an X-ray apparatus, a computed tomography (CT) apparatus, a magnetic resonance imaging (MRI) apparatus, an optical coherence tomography apparatus, an ultrasound imaging apparatus, and a positron emission tomography (PET) apparatus.

4. The system for fabricating an artificial bone tissue of claim 1,
  wherein the server computer is configured to generate the 3D image information of the therapeutic bone tissue model by referring to the first additional information together with the image information of the subject bone tissue, and further configured to generate the second additional information corresponding to the 3D image information of the therapeutic bone tissue model.

5. The system for fabricating an artificial bone tissue of claim 1,
  wherein the server computer includes a first database in which basic image information and supplementary information are stored, the basic image information include image information of normal bone tissues collected from human bodies by age, gender, height, weight, or race, and the supplementary information include at least one of identification information, a disease name, and an operation method related to the normal bone tissues,
  wherein the server computer is configured to detect a first image information of a normal bone tissue corresponding to the image information of the subject bone tissue from the basic image information,
  wherein the server computer is configured to detect a first supplementary information corresponding to the first image information from the supplementary information,
  wherein the server computer is further configured to combine the first image information and the first supplementary information corresponding thereto.

6. The system for fabricating an artificial bone tissue of claim 5, wherein the first database further stores image information related to the subject bone tissue in the past of the patient or image information on the other side normal bone tissue in a bilateral symmetry relationship of the subject bone tissue.

7. The system for fabricating an artificial bone tissue of claim 5,
  wherein the client computer transmits the operation method of the subject bone tissue together with the image information of the subject bone tissue to the server computer,
  wherein the server computer generates the 3D image information of the therapeutic bone tissue model by modifying the image information of the normal bone tissue with reference to the operation method.

8. The system for fabricating an artificial bone tissue of claim 1, wherein the server computer includes a second database for storing information on at least one of a shape, a material, a microstructure, an strength, an operation method, and an operation success rate of the artificial bone tissue.

9. The system for fabricating an artificial bone tissue of claim 1, wherein the client computer is configured to perform edition, comparison, or dimension measurement of a graphical object capable of simulating 3D image information of the therapeutic bone tissue model provided from the server computer through the user interface according to an operation method.

10. The system for fabricating an artificial bone tissue of claim 9, wherein the therapeutic bone tissue model is determined when user accepts or modifies the therapeutic bone tissue model transmitted from the server computer through a result of the simulation.

11. The system for fabricating an artificial bone tissue of claim 9, wherein the client computer includes at least one of an edition tool, a comparison tool, and a dimensional measurement tool of a graphic object for performing the simulation.

12. A computer-based surgical guide system coupled to an imaging unit for imaging a subject bone tissue to generate a 3D image information of the subject bone tissue, and including a user interface for user input or information output, the computer-based surgical guide system comprising:
   a therapeutic bone tissue model generation unit for acquiring a 3D image information of the subject bone tissue from the imaging unit, identifying the subject bone tissue based on the 3D image information of the subject bone tissue, and generating the therapeutic bone tissue model;
   a simulation execution unit for performing a verification on the therapeutic bone tissue model based a user input through a user interface or a recommendation of the therapeutic bone tissue model, and determining the 3D image information of the therapeutic bone tissue model; and
   a machining unit for fabricating an artificial bone tissue from the determined 3D image information of the therapeutic bone tissue model,
   wherein the therapeutic bone tissue model generation unit is configured to acquire a first additional information of a first identification information, a first disease name, and a first operation method of the subject bone tissue together with the 3D image information of the subject bone tissue, the first additional information includes all of the first operation method, the first identification information, and the first disease name, and the first additional information is inputted by a user,
   wherein the therapeutic bone tissue model generation unit is configured to generate a second additional information of a second identification information, a second disease name, and a second operation method which correspond to the therapeutic bone tissue model, the second additional information includes all of the second operation method, the second identification information, and the second disease name, and the second additional information is generated based on the generated 3D image information of the therapeutic bone tissue model,
   wherein the computer-based surgical guide system is configured to provide the user with a comparison result between the first additional information and the second additional information, the comparison result including whether or not there is a match between the first additional information and the second additional information, and the comparison result is used as guide information for recommending a treatment and surgery method for the user.

13. The computer-based surgical guide system of claim 12, wherein the verification of the therapeutic bone tissue model is accomplished through simulation of applying the 3D image information of the therapeutic bone tissue model to the 3D image information of the subject bone tissue.

14. The computer-based surgical guide system of claim 12, wherein the user input includes a command received from a user using at least one of a graphic object editing tool, a comparison tool, or a dimension measurement tool so as to modify the 3D image information of the therapeutic bone tissue model according to an operation method.

15. The computer-based surgical guide system of claim 12, wherein the recommendation of the therapeutic bone tissue model is accomplished by reflecting an information on an operation method among at least one of image information for a pre- or post-procedure of prosthesis, reconstruction, fusion, and diseased area treatment.

16. The computer-based surgical guide system of claim 12,
   wherein the therapeutic bone tissue model generation unit accesses to a first database in which basic image information and supplementary information are stored, the basic image information include image information of normal bone tissues collected from human bodies by age, gender, height, weight, or race, and the supplementary information include at least one of identification information, a disease name, and an operation method related to the normal bone tissues,
   wherein the therapeutic bone tissue model generation unit is configured to detect a first image information of a normal bone tissue corresponding to the image information of the subject bone tissue from the basic image information,
   wherein the therapeutic bone tissue model generation unit is configured to detect a first supplementary information corresponding to the first image information from the supplementary information,
   wherein the therapeutic bone tissue model generation unit is configured to combine the first image information and the first supplementary information,
   wherein the therapeutic bone tissue model generation unit transmits the therapeutic bone tissue model to the simulation execution unit, and the simulation execution unit outputs the therapeutic bone tissue model to the user interface to prepare the verification.

17. A method of fabricating an artificial bone tissue, the method comprising:
   generating a 3D image information of the subject bone tissue by imaging the subject bone tissue, and identifying a first additional information of a first identification information, a first disease name, and a first operation method of the subject bone tissue, wherein the first additional information includes all of the first operation method, the first identification information, and the first disease name, and the first additional information is inputted by a user;
   identifying the subject bone tissue based on at least the 3D image information of the subject bone tissue, and generating a 3D image information of at least one therapeutic bone tissue model corresponding to the subject bone tissue and a second additional information of a second identification information, a second disease name, and a second operation method which correspond to the 3D image information of the at least one therapeutic bone tissue model, wherein the second additional information includes all of the second operation method, the second identification information, and the second disease name, and the second additional information is generated based on the generated 3D image information of the at least one therapeutic bone tissue model;

verifying an adaptiveness of the at least one therapeutic bone tissue model, wherein the verifying of the adaptiveness comprises providing a comparison result between the first additional information and the second additional information to the user, the comparison result including whether or not there is a match between the first additional information and the second additional information, wherein the comparison result is used as guide information for recommending a treatment and surgery method for the user;

determining the 3D image information of the therapeutic bone tissue model in the absence of a modification information on the 3D image information of the at least one therapeutic bone tissue model during the step of verifying;

determining the 3D image information of the therapeutic bone tissue model by reflecting the modification information to the 3D image information of the therapeutic bone tissue model in the presence of the modification information; and fabricating an artificial bone tissue from the determined 3D image information of the therapeutic bone tissue model.

18. The method of fabricating an artificial bone tissue of claim 17, wherein in the step of generating the 3D image information of the therapeutic bone tissue model, the 3D image information of the therapeutic bone tissue model is generated by reflecting at least one of additional information on a prior or a past step of prosthesis, reconstruction, fusion, and diseased area treatment.

19. The method of fabricating an artificial bone tissue of claim 17, wherein in the step of generating the 3D image information of the therapeutic bone tissue model, the 3D image information of the therapeutic bone tissue model is generated by referring to the first additional information together with the 3D image information of the subject bone tissue.

20. The method of fabricating an artificial bone tissue of claim 17,
wherein in the step of generating the 3D image information of the therapeutic bone tissue model, a first database storing basic image information and supplementary information is provided, the basic image information include image information of normal bone tissues collected from human bodies by age, gender, height, weight, or race, and the supplementary information include at least one of identification information, a disease name, and an operation method related to the normal bone tissues,
wherein the method further comprises:
detecting a first image information of a normal bone tissue corresponding to the image information of the subject bone tissue from the basic image information;
detecting a first supplementary information corresponding to the first image information from the supplementary information; and
combining the first image information and the first supplementary information corresponding thereto.

21. The method of fabricating an artificial bone tissue of claim 20,
wherein the 3D image information of the therapeutic bone tissue model is generated by modifying the first image information of the normal bone tissue with reference to the operation method of the first supplementary information.

22. The method of fabricating an artificial bone tissue of claim 17, wherein a second database is provided and the second database stores information on at least one of a shape, a material, a microstructure, a strength, an operation method, and an operation success rate of the artificial bone tissue.

23. The method of fabricating an artificial bone tissue of claim 17, wherein the step of verifying includes simulating the 3D image information of the therapeutic bone tissue model according to an operation method by editing, comparing, or dimension-measuring a graphic object implemented from the 3D image information.

24. The method of fabricating an artificial bone tissue of claim 17, wherein the step of determining the 3D image information of the therapeutic bone tissue model further comprises performing learning by replacing the 3D image information of the normal bone tissue with 3D image information of the replacement bone tissue.

25. The method of fabricating an artificial bone tissue of claim 17, further comprising:
determining a 3D image information of a preliminary artificial bone tissue in a preliminary processing step for forming the therapeutic bone tissue model, after the step of determining the 3D image information of the therapeutic bone tissue model.

26. The method of fabricating an artificial bone tissue of claim 25, wherein the step of fabricating the artificial bone tissue comprising:
preparing a preliminary artificial bone tissue using a 3D image information of the preliminary artificial bone tissue; and
fabricating an artificial bone tissue using a 3D image information of the preliminary artificial bone tissue and the subject bone tissue.

27. The method of fabricating an artificial bone tissue of claim 26, wherein the step of fabricating the preliminary artificial bone tissue is accomplished by performing a preliminary sintering process at a first heat treatment temperature and machining the preliminary artificial bone tissue using the 3D image information of the preliminary artificial bone tissue.

28. The method of fabricating an artificial bone tissue of claim 27,
wherein the step of preparing the artificial bone tissue comprises performing a main sintering process at a second heat treatment temperature,
wherein the second heat treatment temperature is higher than the first heat treatment temperature.

* * * * *